United States Patent [19]
Andrea et al.

[11] Patent Number: 5,916,196
[45] Date of Patent: *Jun. 29, 1999

[54] FLUID DELIVERY SYSTEM FOR A BALLOON CATHETER

[75] Inventors: Martin Andrea, Flurlingen, Switzerland; John Perrins, Leeds, United Kingdom

[73] Assignee: Schneider (Europe) AG, Switzerland

[ * ] Notice: This patent issued on a continued prosecution application filed under 37 CFR 1.53(d), and is subject to the twenty year patent term provisions of 35 U.S.C. 154(a)(2).

[21] Appl. No.: 08/652,282

[22] Filed: May 22, 1996

[30] Foreign Application Priority Data

May 26, 1995 [EP] European Pat. Off. .............. 95107964

[51] Int. Cl.⁶ .................................................. A61M 29/00
[52] U.S. Cl. ........................... 604/97; 604/151; 604/34; 604/30; 604/246; 604/250; 417/474
[58] Field of Search .................................... 606/192, 191, 606/195; 604/96–98, 99–101, 123, 124, 53, 67, 151, 32–34, 104, 280, 22, 30, 48, 118, 119, 246, 248, 249, 250, 131, 121; 128/DIG. 12; 417/474, 476, 477.9–477.13

[56] References Cited

U.S. PATENT DOCUMENTS

| | | | |
|---|---|---|---|
| D. 363,777 | 10/1995 | Rees | D24/146 |
| 3,912,168 | 10/1975 | Mullins et al. | 239/102 |
| 3,994,294 | 11/1976 | Knute | 128/214 |
| 4,332,254 | 6/1982 | Lundquist | 128/344 |
| 4,439,186 | 3/1984 | Kuhl | 604/99 |
| 4,446,867 | 5/1984 | Leveen et al. | 128/344 |
| 4,493,697 | 1/1985 | Krause et al. | 604/50 |
| 4,655,771 | 4/1987 | Wallsten | 623/1 |
| 4,733,665 | 3/1988 | Palmaz | 128/343 |
| 4,762,129 | 8/1988 | Bonzel | 128/344 |
| 4,872,483 | 10/1989 | Shah | 137/557 |
| 4,966,580 | 10/1990 | Turner et al. | 604/67 |
| 5,002,531 | 3/1991 | Bonzel | 604/36 |
| 5,120,303 | 6/1992 | Hombroucky | 604/4 |
| 5,152,776 | 10/1992 | Pinchuk | 606/192 |
| 5,154,700 | 10/1992 | Danby | 604/118 |
| 5,163,421 | 11/1992 | Bernstein et al. | 128/24.1 |
| 5,165,874 | 11/1992 | Sancoff et al. | 417/474 |
| 5,213,483 | 5/1993 | Flaherty et al. | 417/477 |
| 5,232,445 | 8/1993 | Bonzel | 604/36 |
| 5,269,291 | 12/1993 | Carter | 128/24 |
| 5,269,297 | 12/1993 | Weng et al. | 128/24 |
| 5,308,342 | 5/1994 | Sepetka et al. | 604/282 |
| 5,380,273 | 1/1995 | Dubrul et al. | 604/22 |
| 5,382,228 | 1/1995 | Nita et al. | 604/22 |
| 5,409,495 | 4/1995 | Osborn | 606/108 |

(List continued on next page.)

FOREIGN PATENT DOCUMENTS

| | | |
|---|---|---|
| 0276535A1 | 8/1988 | European Pat. Off. . |
| 0363203A3 | 4/1990 | European Pat. Off. . |
| 2533315A1 | 9/1976 | Germany . |
| 3538739A1 | 5/1987 | Germany . |
| 523074 | 5/1972 | Switzerland . |

OTHER PUBLICATIONS

Effect of Low Frequency Vibration of the Arterial Wall, Derek R. Boughner and Margot R. Roach, Circulation Research, vol. XXIX, Aug. 1971, pp. 136–144.

U.S. Patent Application Serial No. 08/826,889, filed apr. 8, 1997, which is owned by Schneider (USA) Inc. Both Schneider (USA) Inc and the Assignee of the above–captioned application are wholly–owned subsidiaries of Pfizer Inc.

*Primary Examiner*—Corrine McDermott
*Assistant Examiner*—Cris L. Rodriguez
*Attorney, Agent, or Firm*—Crompton, Seager & Tufte, LLC

[57] ABSTRACT

The balloon catheter has a portion of its tubular shaft sequentially squeezed between a ram reciprocating in a box and a saddle arranged in a cover closely fitting on the box. The pressurized fluid medium supplied to the balloon is pulsated by the squeeze and release action of the ram and saddle arrangement.

8 Claims, 2 Drawing Sheets

U.S. PATENT DOCUMENTS

| | | | |
|---|---|---|---|
| 5,417,672 | 5/1995 | Nita et al. | 604/283 |
| 5,423,759 | 6/1995 | Campbell | 604/153 |
| 5,427,118 | 6/1995 | Nita et al. | 128/772 |
| 5,439,446 | 8/1995 | Barry | 604/96 |
| 5,447,509 | 9/1995 | Mills et al. | 606/1 |
| 5,451,220 | 9/1995 | Ciervo | 606/1 |
| 5,460,609 | 10/1995 | O'Donnell | 604/100 |
| 5,472,406 | 12/1995 | de la Torre et al. | 601/2 |
| 5,474,530 | 12/1995 | Passafaro et al. | 604/22 |
| 5,498,236 | 3/1996 | Dubrul et al. | 604/22 |
| 5,524,620 | 6/1996 | Rosenschein | 128/653 |
| 5,562,615 | 10/1996 | Nassif | 604/67 |
| 5,611,807 | 3/1997 | O'Boyle | 606/163 |
| 5,658,252 | 8/1997 | Johnson | 604/131 |
| 5,683,367 | 11/1997 | Jordan et al. | 604/118 |
| 5,722,979 | 3/1998 | Kusleika | 606/108 |
| 5,735,817 | 4/1998 | Shantha | 604/100 |
| 5,772,409 | 6/1998 | Johnson | 417/360 |

FLUID DELIVERY SYSTEM FOR A BALLOON CATHETER

BACKGROUND OF THE INVENTION

This invention relates to a system for dispensing to and withdrawing a fluid medium from a balloon catheter for dilatation purposes.

This invention also relates to a stent expansion system comprising a balloon catheter with a tubular shaft having proximal and distal portions, a dilatation balloon mounted on the distal portion of the shaft for expanding an expandable stent, a fluid supply lumen extending throughout the shaft for balloon inflation, and a pressure source for dispensing to and withdrawing a fluid medium from the balloon via the supply lumen.

The invention further relates to a machine for pulsating the medium inflating the balloon of a catheter arrangement having a shaft, a dilatation balloon mounted on the shaft, a fluid supply lumen extending throughout the shaft for balloon inflation, and a pressure source for dispensing to and withdrawing a fluid medium from the balloon via the lumen.

The invention still further relates to a balloon catheter with a tubular shaft having proximal and distal portions, a dilatation balloon mounted on the distal portion of the shaft, and a fluid supply lumen extending throughout the shaft for balloon inflation.

Balloon catheters are quite currently used for dilating vessels or other body cavities. To this end, the balloon is positioned at the area to be dilated and then fed with a fluid medium to achieve dilatation and thereby expand the vessel. During the treatment, the vessel is occluded by the balloon and the blood supply to the upstream organs is interrupted. A further problem is that some occlusions cannot be dilated because the vessel has achieved a rigidity resisting the dilating pressure executed by the balloon.

U.S. Pat. No. 4,439,186 describes a dilatation catheter with an expandable balloon in communication with an inflation lumen extending along the length of the catheter. The balloon has a pressure-volume relationship which is not linear, and a pressure source is provided which supplies a pulsating pressure to the balloon for alternating expansion and contraction thereof. The source of fluctuating pressure comprises a pump supplying a fluid to a container filled with the fluid and which is provided with a flexible bottom connected to the magnetic core of an electromagnet. The container is connected to the dilatation balloon and energizing of the electromagnet causes the magnetic core to move the flexible bottom of the container, thus producing a corresponding pressure pulse or a series of pressure pulses in the fluid within the container. By alternating expansion and contraction of the balloon the blood may circulate during the periods of time during which the vessel is not under action of the balloon. Connection of the container of pressure fluid to the core of an electromagnet requires serious insulation measures in order to avoid any risk of having the patient or other attendant materials in contact with electric current.

U.S. Pat. No. 5,152,776 shows a dilatation balloon catheter fed by a pump controlled by a drive mechanism. The actual fluid conditions present in the balloon are identified by a monitor and communicated to a microprocessor sending orders to the drive mechanism in accordance with a predetermined pattern in order to prevent prolonged cessation of blood flow to sites distal from the action. This structure does not allow the feed of any pulsating pressure to the balloon.

U.S. Pat. No. 4,446,867 shows a fluid driven balloon catheter comprising a catheter with a through going lumen, a fluid supply inflation device attached to one end of the catheter, and a balloon attached to the other end. A pulse generator is provided for generating pressure pulses in the fluid through the lumen to sharply expand and contract the balloon at intervals. This pulse generator comprises a pulse inflation device communicating with the catheter lumen via a T joint and valve, a spring driven ram to bump upon the piston of the pulse inflation device, and a cam rotor to move the ram away from the piston of the pulse inflation device, whereby when the cam moves the ram away from the piston of the pulse inflation device, the spring of the ram is compressed until the cam rotates further and releases the ram to strike the piston of the pulse inflation device. By this pulse action, it is said that the occlusive material in the vessel, which is more brittle than the surrounding vessel wall will crack. However, the friction of the piston in the pulse inflation device of the pulse generator will substantially damp down the pulse action. Furthermore, the hammer operation of the spring loaded ram may cause non negligible stresses on both the piston and pulse inflation device.

The balloon catheter is also an instrument of common use as a mechanism for transporting and applying by expansion a balloon expandable prosthesis, called a stent, for maintaining the patency of a vessel. It is also used for completing the expansion of self-expandable stents which are not transported and applied by a balloon catheter but by a specially devised hollow catheter.

Expansion of a stent requires however a relatively high pressure in the balloon, at least for the last stage force needed to seat or press the stent against the vessel wall. High balloon pressures may induce the risk of overpressure causing trauma to the vessel wall; they also induce the risk of bursting the balloon and further wounding the patient. Furthermore, it is difficult to modulate the pressure in the balloon to precisely control the stent expansion and its embedding into the vessel wall. These difficult conditions need a lot of attention for the expansion manipulation, which is an added load for the practitioner.

There is no suggestion in the documents referred to hereinabove that pulsation of the fluid medium feeding a balloon catheter could be envisaged as a help for stent expansion. Moreover, it has always been considered that a sharp highblow is the way to properly expand and seat a stent in the vessel wall.

It is an object of this invention to propose a fluid delivery for a balloon catheter and a stent expansion system which are highly versatile, simple to manufacture, and easy to use. A further object of the invention is to propose a machine for pulsating the fluid medium inflating the balloon of a balloon catheter arrangement which is highly versatile and very easy to operate, which is simple to manufacture, and which affords a high degree of safety for the patient. Still a further object of the invention is a balloon catheter particularly adapted for a versatile usage.

SUMMARY OF THE INVENTION

In sum, the present invention relates to a system for dispensing and withdrawing a fluid medium to and from a balloon catheter for balloon dilatation purposes, and especially the improvement of means for pulsating the fluid medium when dispensed to the balloon for stepwise expansion of an expandable stent. The stent expansion system may have a balloon catheter with a tubular shaft having proximal and distal portions, a dilatation balloon mounted on the distal portion of the shaft for expanding an expandable stent, a fluid supply lumen extending throughout the shaft for balloon inflation, a pressure source for dispensing and withdrawing a fluid medium to and from the balloon via the supply lumen, and means for pulsating the fluid medium when dispensed to the balloon. The means for pulsating the fluid medium may squeeze the tubular shaft and may sequentially squeeze and release the tubular shaft. The tubular shaft may have in the vicinity of its proximal portion a first region having a first softness and a second region distal of the first region having a second softness, wherein the first softness is greater than the second softness, and wherein the means for pulsating the fluid medium squeeze the tubular shaft in the first region. The tubular shaft may have a third region proximal of the first region, the third region having a softness smaller than that of the first region. The second and third regions may have the same softness. The first region of the tubular shaft may be detachable.

The present invention also relates to a machine for pulsating the fluid medium inflating a balloon of a balloon catheter arrangement. The machine may have a shaft, a dilatation balloon mounted on the shaft, a fluid supply lumen extending throughout the shaft for balloon inflation, a pressure source for dispensing and withdrawing a fluid medium to and from the balloon via the lumen, and saddle means for bearing a portion of the shaft and ram means for squeezing the portion of the shaft against the saddle means. The machine may also have means for reciprocating the cam means towards and away from the saddle means, and the reciprocating means may be motor driven cam means. The machine may also have groove means for positioning the shaft with respect to the ram and saddle means. The machine may also have box means for containing one of the saddle means and ram means, cover means for containing the other of the saddle means and ram means, and means for positioning the cover means on the box means. The machine may also have means for locking the cover means on the box means.

The present invention also relates to a balloon catheter with a tubular shaft having proximal and distal portions, a dilatation balloon mounted on the distal portion of the shaft, and a fluid supply lumen extending throughout the shaft for balloon inflation, wherein the tubular shaft has in the vicinity of its proximal portion a first region having a first softness and a second region distal of the first region and having a second softness, wherein the first softness is greater than the second softness. The first region of the tubular shaft may be detachable. The tubular shaft may be a third region proximal of the first region, the third region having a softness smaller than that of the first region.

The present invention also relates to a medical device having a catheter with a tubular shaft defining a lumen, the catheter having a proximal portion and a distal portion; a balloon mounted on the catheter distal portion and in fluid communication with the lumen; and means for applying force to the catheter shaft at a predetermined location thereby constricting a diameter of the lumen at or about the predetermined location and causing an increase in pressure within the balloon. The means for applying force may be adapted to sequentially squeeze and release the catheter shaft at the predetermined location to cause the balloon to pulsate. The present invention also relates to a method of expanding a stent including delivering a stent to a treatment site, the stent having an interior surface; delivering a balloon catheter to the treatment site, the balloon catheter comprising a tubular shaft defining a lumen, the catheter having a proximal portion and a distal portion, a balloon mounted on the catheter distal portion and in fluid communication with the lumen, and means for applying force to the catheter shaft at a predetermined location thereby constricting a diameter of the lumen at or about the predetermined location and causing an increase in pressure within the balloon, wherein the balloon catheter is delivered such that the balloon is disposed within the stent; and applying force to the catheter shaft at the predetermined location thereby constricting the diameter of the lumen at or about the predetermined location and causing an increase in pressure within the balloon, in turn causing the balloon to apply force to the stent interior surface. The force may be applied by sequentially squeezing and releasing the catheter shaft at the predetermined location causing the balloon to pulsate.

Accordingly, by use of means for pulsating the fluid medium dispensed to the balloon for the stepwise expansion of an expandable stent, as well as by the stent expansion system comprising means for pulsating the fluid medium dispensed to the balloon, the expansion of the stent is achieved by a vibrating strength which causes a succession of very small increments in the radial size of the stent; a better, more uniform and less brutal embedding of the stent in the vessel wall is obtained; the trauma to the vessel wall is reduced and the fluid pressure may be substantially lower than usual.

Where the means for pulsating the fluid medium squeeze the tubular shaft, the pulsation is obtained by action external to the fluid medium, there is no damping of the pulse action, and there is no need for additional fluid containers to be acted upon by electrical equipment. And the means for pulsating the fluid medium may sequentially squeeze and release the tubular shaft without affecting or being affected by the undamped pulse action.

The tubular shaft may comprise in the vicinity of its proximal portion a first region having a first softness and a second region distal of the first region and having a second softness, with the first softness being greater than the second softness and the means for pulsating the fluid medium squeezing the tubular shaft in the first region. A squeeze region is thus created in the tubular shaft which has characteristics different from those of the other portions of the tubular shaft which may thus retain its original characteristics of flexibility, pushability and resistance to kinking.

Where the tubular shaft comprises a third region proximal of the first region and having a softness smaller than that of the first region, the system may be made on the basis of standard catheter elements in which only the first portion has the required softer condition. To further take advantage of standard catheter elements, the second and third regions may have the same softness. And when the first region of the tubular shaft is detachable, the system may be achieved on the basis of a standard catheter shaft with a squeeze portion which may be selected at will, in view of the pulsating conditions which are sought.

As the machine for pulsating the fluid medium comprises saddle means for bearing a portion of the catheter shaft and ram means for squeezing the portion of the tubular shaft against the saddle means, such a machine constitutes a fully independent pulsating equipment for the fluid medium feeding the balloon catheter. There are no stresses on equipment components and no added fluid containers to obtain the pulsation. The balloon catheter may be handled separately for sterilization purposes and the person manipulating the catheter may proceed with sterilized gloves, without handling the machine which may be operated by another person.

Where the machine comprises means for reciprocating the ram means towards and away from the saddle means, a very simple mechanization may be achieved, preferably by means of motor driven cam means. The latter allows easy and rapid change of the pulsation by mere variation of the motor speed or change of the cam means.

The machine may comprise groove means for positioning the shaft with respect to the ram and saddle means, whereby a very simple and fail proof locating of the shaft in the machine.

The machine may comprise box means containing one of the saddle means and ram means, cover means for containing the other of the saddle and ram means, and means for positioning the cover means on the box means, with the possibility of having means for locking the cover means on the box means. This results in a closed, self-contained, error proof unit which can be permanently placed in an appropriate location of the operating room or which can be brought in any convenient place in the operating room to be available upon need of pulsating the fluid medium in a balloon catheter.

As the tubular shaft of the balloon catheter comprises in the vicinity of its proximal portion a first region having a first softness and a second region distal of the first region and having a second softness, with the first softness being greater than the second softness, the balloon catheter is particularly adapted to having its first region squeezed for pulsating the fluid medium used to feed the balloon. And where this first region is detachable and/or preceded by a third region having a smaller softness, use can be made of a standard catheter with attachment of the region specifically adapted to squeeze pulsation.

DESCRIPTION OF THE DRAWINGS

These and other objects of the invention will become readily apparent from the following detailed description with reference to the accompanying drawings which show, diagrammatically and by way of example only, one embodiment illustrating the invention.

DETAILED DESCRIPTION OF THE INVENTIONS

Figure 1:
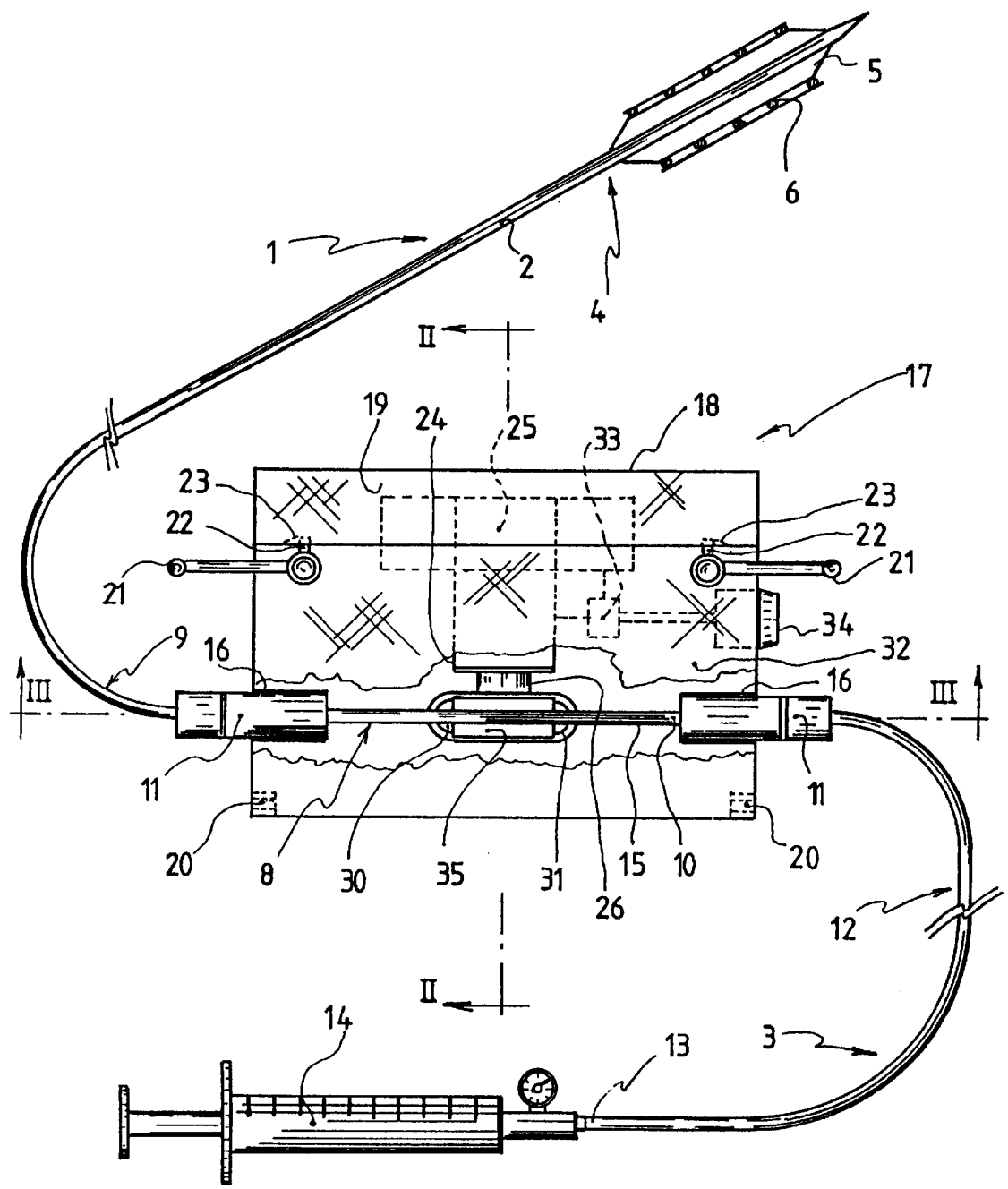
FIG. 1 is a partly cut upper plan view of a stent expansion system and pulsating machine.
Figure 2:
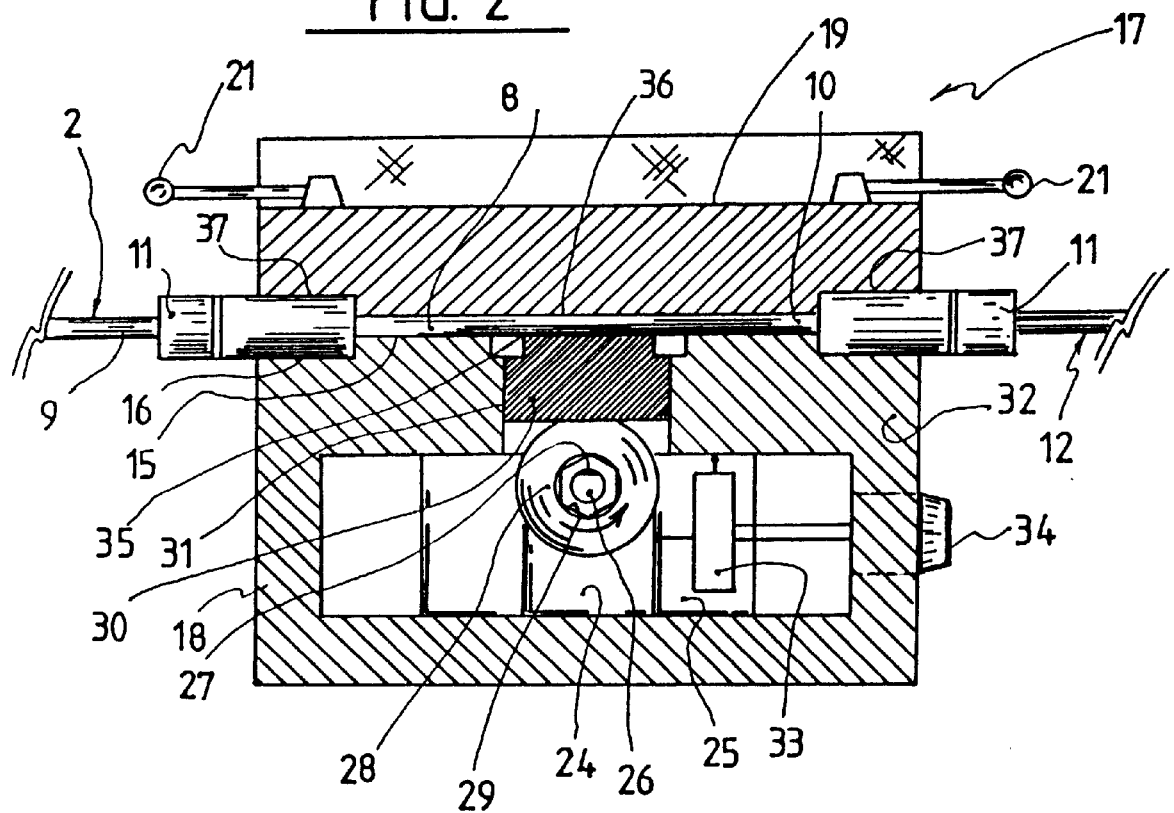
FIG. 2 is a part section according to line II—II of FIG. 1.
Figure 3:
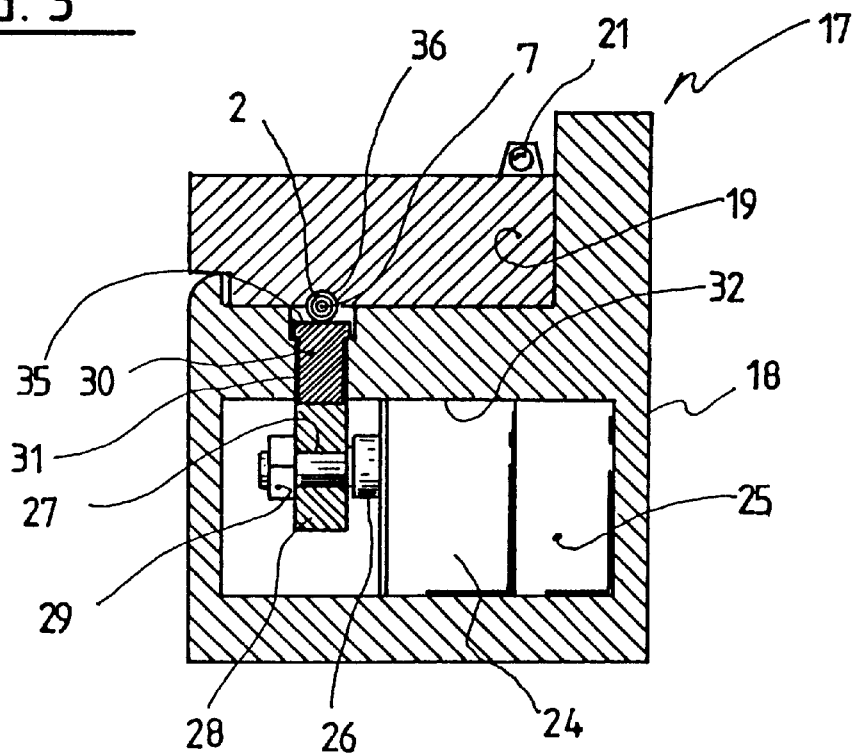
FIG. 3 is a part section according to line III—III of FIG. 1.

The stent expansion system shown in FIGS. 1 to 3 comprises a balloon catheter 1 with a tubular shaft 2 having proximal and distal portions 3 and 4 respectively. A dilatation balloon 5 is mounted on the distal portion 4 of shaft 2, e.g., for expanding an expandable stent 6. A fluid supply lumen 7, visible on FIG. 3, extends throughout the shaft 2 and this fluid supply lumen is fed by a pressure source (inflation device 14) for dispensing to and withdrawing from the balloon a fluid medium.

In the vicinity of its proximal portion 3, the catheter shaft 2 comprises a first region 8 having a first softness and a second region 9 distal of first region 8 and having a second softness, with the softness of first region 8 being greater than the softness of second region 9. The first region 8 is formed by a piece of catheter shaft 10 detachably connected, via standard shaft connectors 11, between the second region 9 of the catheter shaft and a third region 12 of the catheter shaft proximal of the first region 8, the third region 12 having, preferably, a softness smaller than the softness of first region 8. In order to be made of the same catheter material, the second and third regions 9 and 12 may have the same softness.

The proximal end 13 of the tubular shaft 2 is connected to the inflation device 14 for feeding the balloon 5 with a fluid medium under pressure.

The first region 8 of the tubular shaft 2 and the connectors 11 are respectively located in the positioning grooves 15 and 16 of a machine 17 for pulsating the fluid medium inflating the balloon 5 of balloon catheter 1.

This machine comprises a box 18 in which are arranged the grooves 15 and 16 and a cover 19 pivotally mounted as shown by pivots 20. The cover comprises two pivotal handles 21 having each a lock 22 adapted to fit in a catch 23 devised in box 18 for rapid and precise closure of cover 19 over box 18.

Inside the box 18 is arranged an electrical rotary motor 24 connected to a source of power such as, for instance, a rechargeable battery 25 also located inside the box 18. Rotation of the motor 24 is controlled by a regulator 33 the control knob 34 of which is located on a lateral wall of box 18.

Motor 24 drives a shaft 26 the end of which comprises a flat portion 27 for driving an eccentric-wheel or cam 28 mounted thereon and secured by a nut 29 screwed on the end of shaft 26. Eccentric wheel 28 drives a ram 30 mounted for reciprocal motion in a vertical groove 31 arranged in the upper wall 32 of box 18. Vertical groove 31 opens into an enlargement in which extends the top 35 of ram 30. The enlargement of vertical groove 31 opens into groove 16. The cover 19 comprises positioning grooves 36 and 37 respectively corresponding to and facing positioning grooves 15 and 16 devised in box 18 for positioning the first region 8 and connectors 11 of the tubular shaft 2. By this arrangement, top 35 of ram 30 faces groove 36 of cover 19 which may act as a saddle for the first region 8 of tubular shaft 2 when the latter is positioned into grooves 15 and 36 of box 18 and cover 19, with cover 19 abated on box 18 and locked thereon by locks and catches 22 and 23.

Operation of this material may be as follows: the balloon catheter 1 with its shaft 2 and the inflation device 14, which are totally independent from the machine 17, may be sterilized and handled by an operator wearing sterilized gloves, whereas the machine 17, including handling of cover 19 and control of motor 24, may be handled by another operator.

When the catheter shaft is positioned into grooves 15 and 36, respectively 16 and 37, of box 18 and cover 19, the motor 24 may be energized to rotate the cam or eccentric-wheel 28 which reciprocates ram 30 the top 35 of which consequently squeezes and relaxes the first region 8 of tubular shaft 2 against and from the saddle or groove 36. When the inflation device 14 feeds the balloon 5 with fluid under pressure, there is a base pressure within the tubular shaft 2 and balloon 5. Hence, squeeze and release of the catheter shaft by ram 30 and saddle 36 create an overpressure in the catheter shaft followed by a return to base pressure, thereby pulsating the fluid medium. Frequency of the pulsating condition may be adjusted by varying the speed of rotation of motor 24 via regulator 33.

Variants can be envisaged: for example, the two handle locking of cover 19 on box 18 may be replaced by a one handle locking. The motor 24 may be energized by direct connection to the mains. The inflation device 14 may be replaced by a motorized pump. The system may be used for vessel dilatation, i.e., without stent expansion; similarly, the machine 17 may be used for pulsating the fluid medium inflating the balloon for stenosis dilatation, not necessarily followed by a stent deployment. Depending on the characteristics of the tubular shaft 2, it may be possible to avoid the three region arrangement described; similarly, the first region 8 may be extended up to the inflation device 14, thereby avoiding use of the third region 12.

Of course, the technology herein described also fully applies to self-expandable stents which are not delivered by a balloon catheter but by a specifically devised hollow catheter from which the stent is deployed for self-expansion. With such stents, an additional balloon expansion is currently performed to complete or help completing the embedding of the stent in the vessel. All documents cited herein are incorporated herein in their entireties for all purposes.

We claim:

1. A medical device comprising:
   (a) a catheter having a tubular shaft defining a lumen, the catheter having a proximal portion and a distal portion;
   (b) a balloon mounted on the catheter distal portion and in fluid communication with the lumen; and
   (c) a repetitive force applying element associated with the catheter shaft which compresses the outside of the catheter shaft at a predetermined location thereby causing vibration within the balloon.

2. The device of claim 1 wherein the repetitive force applying element is adapted to sequentially squeeze and release the catheter shaft at the predetermined location therealong to cause the balloon to pulsate.

3. The medical device of claim 1 wherein the tubular shaft comprises in the vicinity of its proximal portion a first region having a first softness and a second region having a second softness, wherein the first softness is greater than the second softness, and wherein the repetitive force applying element compresses the tubular shaft in the first region.

4. A stent expansion system comprising:
   (a) a balloon catheter with a tubular shaft having a proximal portion and a distal portion;
   (b) a dilatation balloon mounted on the distal portion of the shaft;
   (c) an expandable stent disposed at least partially about the dilatation balloon for expanding the expandable stent;
   (d) a fluid supply lumen extending throughout the shaft for balloon inflation;
   (e) a pressure source for dispensing a fluid medium to the balloon via the supply lumen;
   (f) means for pulsating the dispensed fluid medium when dispensed to the balloon during inflation;
   (g) a tubular shaft saddle means portion on the means for pulsating the dispensed fluid to receive the tubular shaft, the tubular shaft saddle means for bearing a portion between the proximal portion and the distal portion of the tubular shaft, and
   (h) ram means located on the means for pulsating the dispensed fluid, the ram means aligned for reciprocal movement for squeezing the portion of the tubular shaft against the saddle means so the balloon is inflated in stages with pulsed fluid.

5. The stent expansion system of claim 4 wherein the tubular shaft comprises a third region proximal of the first region, and wherein the third region has a softness smaller than that of the first region.

6. The stent expansion system of claim 5 wherein the second and third regions have the same softness.

7. The stent expansion system of claim 4 wherein the first region of the tubular shaft is detachable.

8. The stent expansion system of claim 4 wherein the tubular shaft includes in the vicinity of its proximal portion a first region having a first softness and a second region distal of the first region and having a second softness, wherein the first softness is greater than the second softness, and wherein the means for pulsating the fluid medium squeezes the tubular shaft in the first region.

* * * * *